United States Patent
Nagashima et al.

(10) Patent No.: US 10,271,542 B2
(45) Date of Patent: Apr. 30, 2019

(54) HOLLOW FIBER CRYOPRESERVATION INSTRUMENT AND CELL CRYOPRESERVATION METHOD

(71) Applicant: Meiji University, Tokyo (JP)

(72) Inventors: Hiroshi Nagashima, Kawasaki (JP); Hitomi Matsunari, Kawasaki (JP); Ayuko Uchikura, Kawasaki (JP)

(73) Assignee: Meiji University, Tokyo (JP)

( * ) Notice: Subject to any disclaimer, the term of this patent is extended or adjusted under 35 U.S.C. 154(b) by 0 days.

(21) Appl. No.: 15/541,772

(22) PCT Filed: Dec. 28, 2015

(86) PCT No.: PCT/JP2015/086462
§ 371 (c)(1),
(2) Date: Jul. 6, 2017

(87) PCT Pub. No.: WO2016/111217
PCT Pub. Date: Jul. 14, 2016

(65) Prior Publication Data
US 2018/0000067 A1   Jan. 4, 2018

(30) Foreign Application Priority Data
Jan. 9, 2015   (JP) .................... 2015-003070

(51) Int. Cl.
*A01N 1/02*   (2006.01)
*C12N 1/04*   (2006.01)

(52) U.S. Cl.
CPC ......... *A01N 1/0268* (2013.01); *A01N 1/0284* (2013.01); *C12N 1/04* (2013.01)

(58) Field of Classification Search
CPC .................................................. A01N 1/0268
See application file for complete search history.

(56) References Cited

U.S. PATENT DOCUMENTS 7,435,582 B2   10/2008   Zimmermann et al.

FOREIGN PATENT DOCUMENTS

| EP | 2140814 A1 | 1/2010 |
| JP | 2009148221 A | 7/2009 |
| JP | 2010213692 A | 9/2010 |
| JP | 5278978 B | 9/2013 |

(Continued)

OTHER PUBLICATIONS

McLaughlin et al., A comparison of the freezing of human semen in the uncirculated vapour above liquid nitrogen and in a commercial semi-programmable freezer. Human Reproduction, vol. 5, No. 6 (Aug. 1, 1990) pp. 724-728. (Year: 1990).*

(Continued)

*Primary Examiner* — Kara D Johnson
(74) *Attorney, Agent, or Firm* — Wood Herron & Evans LLP (57) ABSTRACT

Provided are 1) a hollow fiber cryopreservation instrument having a long support on which a hollow fiber is placed, wherein the support is formed of a low-temperature-resistant material, and 2) a cell cryopreservation method having a process of placing a hollow fiber on the support of the hollow fiber cryopreservation instrument, and a process of cryopreserving cells in a state in which the hollow fiber is placed on the support.

15 Claims, 10 Drawing Sheets

(56) References Cited

FOREIGN PATENT DOCUMENTS

| WO | 2006059626 A1 | 6/2006 |
|---|---|---|
| WO | 2010046949 A1 | 4/2010 |

OTHER PUBLICATIONS

Straw Technique. Datasheet [online]. Veterinary Andrology and Reproductive Techniques, 2012 [retrieved on May 16, 2018]. Retrieved from the Internet: <URL: http://ecoursesonline.iasri.res.in/mod/page/view.php?id=153934>. (Year: 2012).*
'Fresh Chilled and Frozen Semen'. Services Provided [online]. VetCor Canine Reproductive Services, 2011 [retrieved on May 22, 2018]. Retrieved from the Internet: <URL: http://www.vetcor.ca/VetCor/Semen.html>. (Year: 2011).*
European Patent Office, Search Report issued in European Patent Application No. 15877089.1 dated Oct. 5, 2018, 10 pages.
H. Matsunari et al., Journal of Reproduction and Development, vol. 58 (2012) 599-608.
J. Mizuno et al., Development of a Low Toxicity and Serum-Free Vitrification System for ART: Using a Cryo-Nano-Hole Vitrification Container, Journal of Fertilization and Implantation, 2009, vol. 26, No. 1, p. 32-40.
PCT Office, International Search Report issued in PCT/JP2015/086462 dated Feb. 16, 2016, 3 pages.
PCT Office, International Preliminary Report on Patentability issued in PCT/JP2015/086462 dated Nov. 8, 2016, 10 pages.

* cited by examiner

HOLLOW FIBER CRYOPRESERVATION INSTRUMENT AND CELL CRYOPRESERVATION METHOD

TECHNICAL FIELD

The present invention relates to a hollow fiber cryopreservation instrument used to cryopreserve a hollow fiber, and a cell cryopreservation method for cryopreserving a hollow fiber, in an internal space of which cells are included, and preserving the cells.

Priority is claimed on Japanese Patent Application No. 2015-003070, filed on Jan. 9, 2015, the contents of which are incorporated herein by reference.

BACKGROUND ART

As a method of preserving a cell, a method of freezing and preserving a cell, such as a low-temperature preserving method or an ultralow-temperature preserving method, is generally performed. As a freezing method, both a slow freezing method and a vitrification freezing method are well known. The slow freezing method cools a cell at a slow cooling rate for a long time, and inhibits the formation of large ice crystals in the cell. Thereby, damage (freezing damage) to the cell due to freezing is assumed to be avoidable. However, the slow freezing method requires a long time until freezing is completed, and requires the use of an expensive freezer or the like having a special function to control the cooling rate. As an alternative method to overcome the disadvantages in the slow freezing method, a vitrification freezing method has been widely used in recent years. The vitrification freezing method is a method of quickly freezing a cell processed with a vitrification solution using liquid nitrogen and thereby freezing the cell without forming ice crystals inside and outside the cell. This uses a phenomenon called vitrification, that is, a phenomenon in which, when a solution is rapidly cooled, the solution quickly passes through an original freezing point to cause supercooling, and movement of water molecules comes to a stop without forming ice crystals. This method is assumed to be superior to the slow freezing method in that damage to the cell caused by formation of ice crystals does not occur, in that a time required for processing is short, and in that a special equipment is not required. Multiple specific vitrification freezing methods for the cell have been developed. As one example, there is a method of dipping the cell into a freezing-resistant preserving solution and rapidly freezing in liquid nitrogen or in an ultralow freezer.

In cryopreservation of an ovum, cryopreservation using an exclusive instrument is performed. For example, as an exclusive instrument that is currently used in a cryopreservation method of the ovum, there is a Cryotop (registered trademark). Cryotop is an exclusive instrument (Cryotop) in which an extremely thin strip-like sheet is attached to a tip of a handle. Generally, the cryopreservation method using Cryotop is called a Cryotop method. In the Cryotop method, for example, a freezing fluid including a cryoprotectant and an ovum are placed on the sheet of the Cryotop, and the sheet on which the ovum is placed is dipped into liquid nitrogen and is vitrified and frozen. Then, the sheet is housed and protected in a sheath-like container to protect a sheet portion, and is kept in the liquid nitrogen or the freezer.

The inventors of the present invention have recently developed a hollow fiber cryopreservation method which is a cell cryopreservation method (Non-Patent Literature 1). This is a method of introducing a cell such as an egg cell into a hollow fiber made of a cellulose acetate membrane and cryopreserving the cell in a state in which the egg cell is included in the hollow fiber. The hollow fiber cryopreservation method is a highly reliable method capable of improving cell viability, and dissemination thereof is eagerly anticipated.

CITATION LIST

Non-Patent Literature

Non-Patent Literature 1

H. Matsunari, M. Maehara, K. Nakano, Y. Ikezawa, Y. Hagiwara, N. Sasayama, A. Shirasu, H. Ohta, M. Takahashi, H. Nagashima. Journal of Reproduction and Development, Vol. 58 (2012) 599-608

SUMMARY OF INVENTION

Technical Problem

In the cryopreservation of the cell, the cell is cryopreserved in liquid nitrogen. However, when the cell is put into liquid nitrogen as it is, there is a possibility of bacterial contamination or the like. Bacterial contamination includes, for example, a case in which, when a cell infected with bacteria is put into liquid nitrogen, bacteria discharged from the cell contaminate the liquid nitrogen and are adhered to another cell via the contaminated liquid nitrogen. To cryopreserve a highly scarce sample such as an ovum, there is a need to avoid this contamination as much as possible. For this reason, the ovum is housed in a sheath-like container in a sealed state, and it is preferable to cryopreserve the ovum in this state. This is because the sheet portion is housed in the sheath-like container in the Cryotop method and then is put into liquid nitrogen.

However, since a hollow fiber is a relatively brittle material, when the hollow fiber is picked up with tweezers and is housed in a container for cryopreservation as it is, there is a possibility that the container for cryopreservation and the hollow fiber come into contact with each other, and the hollow fiber is broken. Advantages of the hollow fiber cryopreservation method have already been reported. However, the hollow fiber is difficult to handle, for example, is easily broken, and a user thereof is limited to a skilled researcher.

The inventors also devised a technique for introducing a hollow fiber into a container for cryopreservation, a part of which is immersed in liquid nitrogen while holding the hollow fiber with tweezers in order to more effectively inhibit bacterial contamination or the like, and freezing the hollow fiber. Even in this technique, since the hollow fiber is a light and relatively brittle material, a user thereof is limited to a skilled researcher for the same reasons as above.

The absence of an adequate instrument for cryopreserving a hollow fiber in this way also hinders the dissemination of a hollow fiber cryopreservation method.

The inventors have realized that a support instrument is required for hollow fiber cryopreservation which makes it possible to hold a hollow fiber and to easily handle the hollow fiber.

The present invention was conceived in view of the above circumstances, and provides a hollow fiber cryopreservation instrument capable of easily cryopreserving a hollow fiber, and a cell cryopreservation method capable of easily cryopreserving the hollow fiber, in an internal space of which cells such as germ cells are included.

Solution to Problem

The present invention provides a hollow fiber cryopreservation instrument and a cell cryopreservation method having the following features.

(1) A hollow fiber cryopreservation instrument including a long support on which a hollow fiber is placed, wherein the support is formed of a low-temperature-resistant material.

(2) The hollow fiber cryopreservation instrument according to (1), wherein through-holes passing through a side on which a hollow fiber is placed and a side opposite to the side on which the hollow fiber is placed are formed in the support.

(3) The hollow fiber cryopreservation instrument according to (2), wherein the through-holes are formed in nearly the middle of the support in a longitudinal direction of the support.

(4) The hollow fiber cryopreservation instrument according to any one of (1) to (3), wherein the support has a bottom part on which the hollow fiber is placed, and sidewall parts that rise from the bottom part in a longitudinal direction of the support.

(5) The hollow fiber cryopreservation instrument according to any one of (1) to (4), wherein the support is made of a resin or a metal.

(6) A cell cryopreservation method including:
a process of placing the hollow fiber, in an internal space of which cells are included, on the support of the hollow fiber cryopreservation instrument according to any one of (1) to (5); and
a process of cryopreserving the cells in a state in which the hollow fiber is placed on the support.

(7) The cell cryopreservation method according to (6), wherein the cell cryopreservation method includes a process of storing the support, on which the hollow fiber is placed, in a protective container after the process of placing the hollow fiber on the support.

(8) The cell cryopreservation method according to (6) or (7), wherein the cell cryopreservation method includes a process of cooling the hollow fiber to freeze the cells after the process of placing the hollow fiber on the support.

(9) The cell cryopreservation method according to any one of (6) to (8), wherein the cells are germ cells and/or stem cells.

Advantageous Effects of Invention

According to the present invention, a hollow fiber cryopreservation instrument and a cell cryopreservation method capable of easily cryopreserving a hollow fiber can be provided.

DESCRIPTION OF EMBODIMENTS

«Cell Culture Substrate»

A hollow fiber cryopreservation instrument of the present invention includes a long support on which a hollow fiber is placed wherein the support is formed of a low-temperature-resistant material. Hereinafter, the hollow fiber cryopreservation instrument of the present embodiment will be described by way of example with reference to the drawings. The hollow fiber cryopreservation instrument of the present invention is not limited to the following embodiments.

First Embodiment

A hollow fiber cryopreservation instrument of the present embodiment includes a long support on which a hollow fiber is placed.

The term hollow fiber refers to cells that can be included in an internal space thereof and a membrane having a plurality of holes having diameters that do not allow the passage of target cells but allow the passage of water, an electrolyte, a protein, and so on is molded in a straw shape. The membrane forming the hollow fiber includes polysulfone, polyethersulfone, polyacrylonitrile, polyamide, polyethylene, polypropylene, cellulose acetate, regenerated cellulose, or the like. The diameters of the fine holes, which the membrane has, are preferably diameters on the order of nanometers. In order for the hollow fiber to have a degree of transparency as to enable observation of the above germ cells, a thickness of the membrane preferably ranges from 0.5 µm to 30 µm, and more preferably from 1 µm to 10 µm.

The inner diameter of the hollow fiber is selected from inner diameters that allow the target cells to be contained, preferably ranging from 20 µm to 1000 µm, and more preferably from 50 µm to 500 µm.

The length of the hollow fiber can preferably contain several cells, and is selected from lengths suitable for forming bubbles described in, for example, U.S. Pat. No. 5,051,716. The length of the hollow fiber preferably ranges from 1 mm to 100 mm, and more preferably from 10 mm to 40 mm. If the length of the hollow fiber is within this range, the hollow fiber can contain one to dozens of oocytes, ova, or early embryos. According to the method described in, for example, U.S. Pat. No. 5,051,716, a hollow fiber can contain dozens to tens of thousands of primordial germ cells, spermatozoa, or sperm cells, and bubbles can be formed around opposite openings of the hollow fiber with respect to the plurality of contained germ cells.

Figure 1:
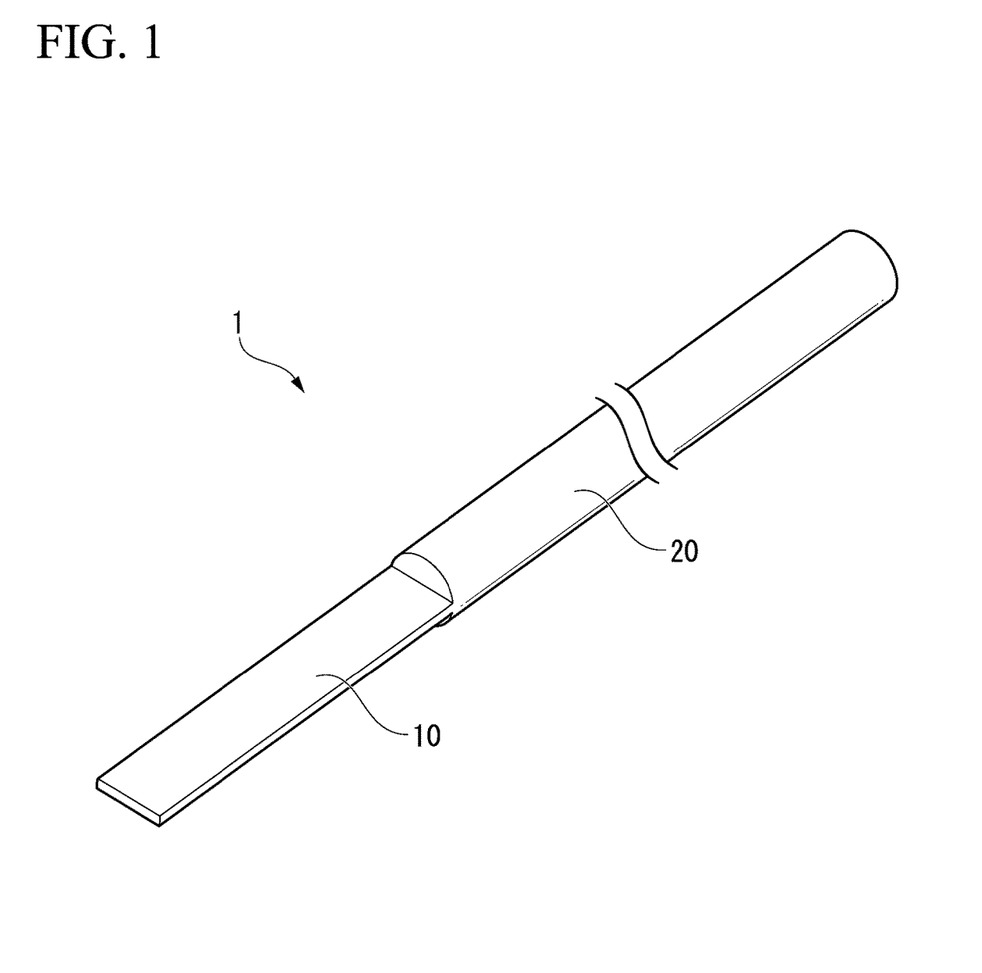
FIG. 1 is a perspective view illustrating an embodiment of a hollow fiber cryopreservation instrument according to the present invention.

FIG. 1 is a perspective view illustrating an embodiment of a hollow fiber cryopreservation instrument according to the present invention. A hollow fiber cryopreservation instrument 1 includes a long support 10 on which a hollow fiber is placed. A rod-like handle 20 serving as a handle is formed at one end of the support 10.

The support 10 is formed in a rectangular plate shape. The length of the support 10 is preferably a length that is longer than the length of the hollow fiber, in the internal space of which the cells are included, and is preferably set to a range from 0.5 cm to 5 cm by way of example. The width of the support 10 is preferably formed to be wider than the hollow fiber, in the internal space of which the cells are included, and is preferably formed within a range from 0.1 cm to 1 cm.

In using the hollow fiber cryopreservation instrument, it is assumed that, after the hollow fiber, in the internal space of which the cells are included, is placed on the support 10, a task of cooling the hollow fiber along with the support 10 is performed (see FIG. 7 or the like to be described below). At this time, since the hollow fiber is typically coated with a cryopreserving solution, when the hollow fiber and the support are cooled, the cryopreserving solution and the hollow fiber are integrated, and the hollow fiber is fixed to the support 10. Therefore, flexure of the support 10 generates flexure of the hollow fiber. For this reason, the support 10 preferably exhibits rigidity to such an extent that the support 10 is neither easily deformed by a slight load nor damages the hollow fiber.

In addition, in using the hollow fiber cryopreservation instrument, it is assumed that, after the hollow fiber, in the internal space of which the cells are included, is placed on the support 10, a task of storing the support, on which the hollow fiber is placed, in a tubular protective container is performed (see FIG. 10 or the like to be described below). When this task is performed, for example, even when the support 10 and the protective container 40 are brought into contact with each other and a slight load is applied to the support 10, the support 10 preferably exhibits rigidity to such an extent that the support 10 is not deformed to damage the hollow fiber.

The support 10 may be formed of a low-temperature-resistant material. The low-temperature-resistant material refers to a material in which it is difficult to generate a low-temperature fracture when cryopreserved. The low-temperature-resistant material may be a material that has low-temperature resistance to such an extent that it is hardly embrittled and damaged even if is immersed in either a low-temperature or ultralow-temperature vapor atmosphere or liquid nitrogen and, for example, may be a resin or a metal.

Here, the low-temperature vapor atmosphere indicates a vapor atmosphere of −20° C. to −269° C., and the ultralow-temperature vapor atmosphere indicates a vapor atmosphere of −80° C. to an absolute zero point, and includes, for example, a low-temperature or ultralow-temperature nitrogen vapor atmosphere or the inside of a freezer.

In addition, in using the hollow fiber cryopreservation instrument, it is assumed that a task of heating the hollow fiber, in the internal space of which the cells are included, along with the support 10 is performed. At this time, instantaneous heating of the cells included in the hollow fiber by instantaneously raising a temperature of the hollow fiber may be preferred according to a cell state.

The metal includes, but is not limited to, for example, titanium, aluminum, stainless steel, or the like. The resin may be a synthetic resin or a natural resin. The synthetic resin includes, but is not limited to, polyvinyl chloride, polyester, polyimide, polysulfone, polystyrene, polyvinyl acetate, polystyrene, polyurethane, an ABS resin, an AS resin, an acrylic resin, polyethylene, polypropylene, polycarbonate, a fluororesin such as polytetrafluoroethylene, or the like. Among the aforementioned synthetic resins, polycarbonate is preferred.

A thickness of the support 10 is not particularly limited. When the support 10 is made of a resin or a metal, the thickness of the support 10 is preferably formed to 0.01 mm or more, more preferably 0.1 mm or more, and most preferably 0.3 mm or more in consideration of imparting rigidity to the support 10 to such an extent that the hollow fiber is not damaged.

As described above, in using the hollow fiber cryopreservation instrument, it is assumed that the task of heating the hollow fiber, in the internal space of which the cells are included, along with the support 10 is performed. At this time, instantaneous heating of the cells included in the hollow fiber by instantaneously raising the temperature of the hollow fiber may be preferred according to the cell state. When a heat capacity of the support 10 is high in performing this task, there is a possibility of transferring the coldness of the support 10 to the hollow fiber and preventing the hollow fiber and the cells from being instantaneously heated.

Therefore, the thickness of the support 10 is not particularly limited. However, when the support 10 is made of a resin or a metal, the thickness of the support 10 is preferably formed to 0.01 mm or more and 1 mm or less, more preferably 0.1 mm or more and 0.7 mm or less, and most preferably 0.3 mm or more and 0.5 mm or less.

When comparing heat capacities per the same volume, the metal is typically higher than the resin. When the resin and the metal are compared, the resin is more preferred.

As a support instrument for cryopreserving the hollow fiber, there is an absence of a commercially available exclusive instrument. However, when the hollow fiber is configured to be placed on the commercially available exclusive instrument for cryopreserving the cells, since it is not considered to place the hollow fiber, a length of a sheet portion is short, and the hollow fiber cannot be successfully loaded. Since the sheet portion is made to be very thin, there is a problem in that a sheet is bent, for instance, when the sheet portion is put into a container, and the hollow fiber is easily broken.

In contrast, according to the hollow fiber cryopreservation instrument 1 of the present embodiment, the support 10 has a shape suitable for placing the hollow fiber, and the support 10 is not greatly bent even when the hollow fiber is placed on the support 10 and is used, there is a low possibility of doing damage to the cells included in the hollow fiber, and the cells can be simply cryopreserved.

Second Embodiment

A hollow fiber cryopreservation instrument of the present embodiment includes a long support on which a hollow fiber is placed. The support is formed of a low-temperature-resistant material. The support has a bottom part for placing the hollow fiber, and sidewall parts that rise from the bottom part in a longitudinal direction of the support. A description is not given of items in common with the hollow fiber cryopreservation instrument of the first embodiment.

Figure 2:
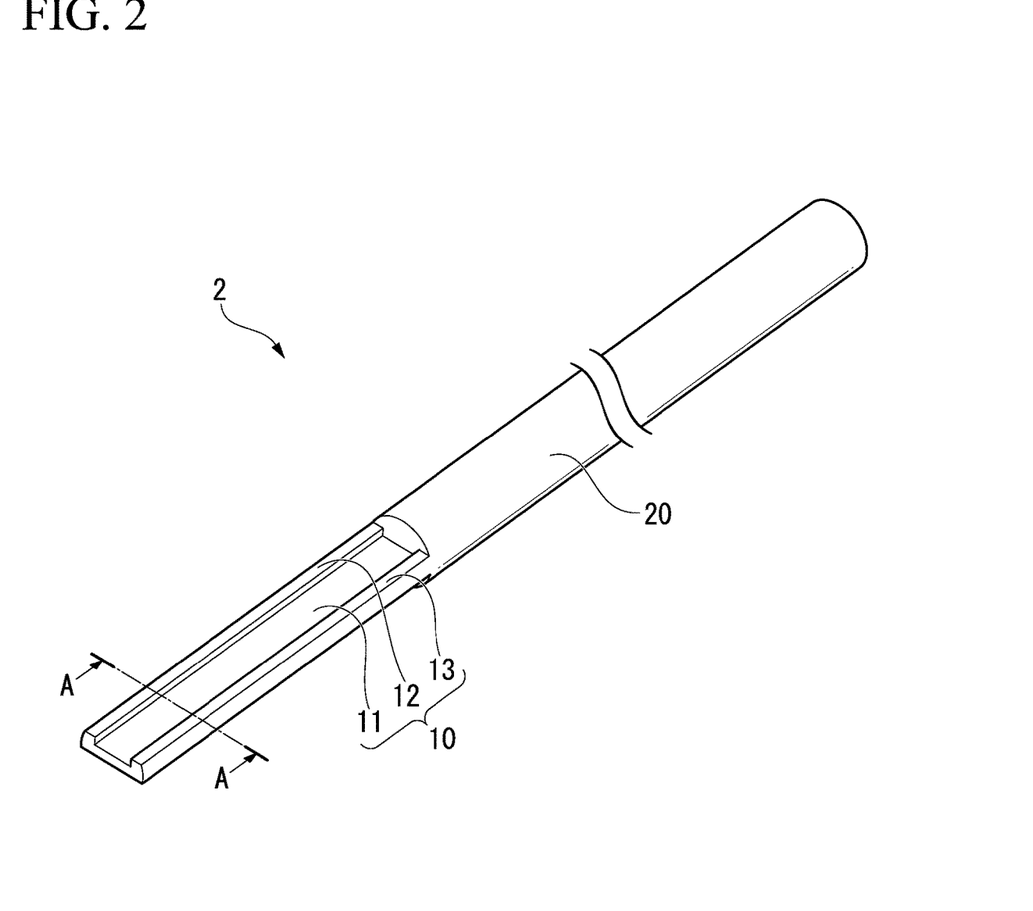
FIG. 2 is a perspective view illustrating an embodiment of the hollow fiber cryopreservation instrument according to the present invention.

FIG. 2 is a perspective view illustrating an embodiment of a hollow fiber cryopreservation instrument according to the present invention. A hollow fiber cryopreservation instrument 2 includes a long support 10 on which a hollow fiber is placed. A rod-like handle 20 serving as a handle is formed at one end of the support 10. The support 10 has a bottom part 11, and sidewall parts 12 and 13 that rise from the bottom part in a longitudinal direction of the support.

As illustrated in FIG. 2, the sidewall parts 12 and 13 are preferably formed at both ends of the support 10 in a transverse direction of the support 10. When the hollow fiber is placed on the bottom part 11 of the support 10, the sidewall parts 12 and 13 formed at both ends of the bottom part 11 become guides for the hollow fiber, and prevent the hollow fiber from protruding from the support. After the hollow fiber, in an internal space of which cells are included, is placed on the support 10, when the support on which the hollow fiber is placed is stored in a tubular protective container, the hollow fiber can be more favorably stored in the protective container because contact between the hollow fiber and the protective container material is prevented.

Further, the support 10 has the sidewall parts 12 and 13, and thereby rigidity of the entire support can be improved. As illustrated in FIG. 2, the sidewall parts 12 and 13 are formed at the support 10, and thereby the rigidity of the entire support is improved. For this reason, in comparison with the support 10 without the sidewall parts, a thickness of the bottom part 11 on which the hollow fiber can be placed can be set to be thinner. The thickness of the bottom part 11 is thinned, and thereby the cells included in the hollow fiber can be more quickly cooled or heated.

Figure 3:
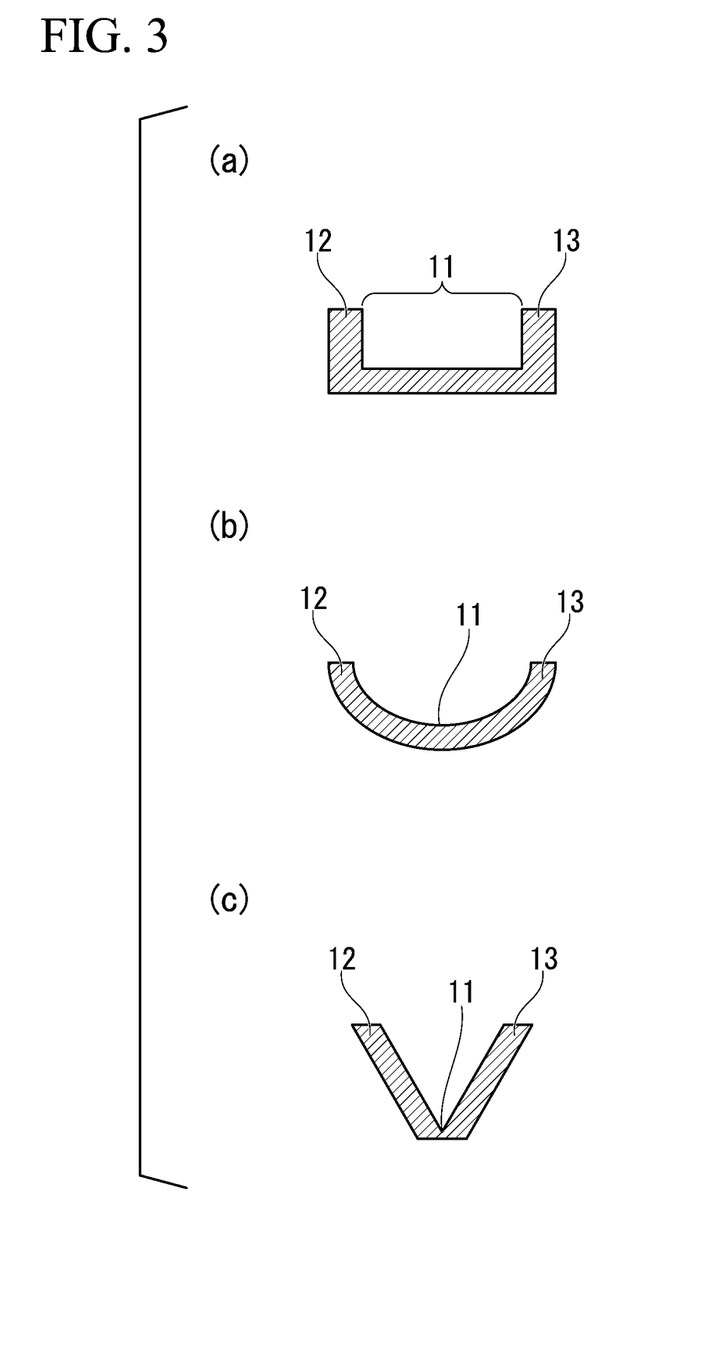
FIG. 3 is a sectional view illustrating an embodiment of the hollow fiber cryopreservation instrument according to the present invention.

FIG. 3(a) is a sectional view taken along line A-A of FIG. 2. In the present embodiment, as illustrated in FIG. 3(a), the support in which the bottom part and the sidewall parts are connected to cross at right angles and a cross-sectional shape is a U shape is given as an example. As illustrated in FIGS. 3(b) and 3(c), as other shapes of the supports, a support having a recessed cross-sectional shape such as a C shape, a V shape, a shape of a figure made up of a trapezoidal leg and an upper bottom, or the like can be given as an example. The recessed cross-sectional shape includes a shape in which a dent part is present in the center of the cross section of the support, and a shape in which a dent part is closer to an end than the center of the cross section of the support. In the shape of the cross section of the support, there is no limitation to a ratio of length between the bottom part and the sidewall part, and an angle formed by the bottom part and the sidewall parts. In the shape of the cross section of the support, there is also no limitation to shapes (for example, whether a straight line or a curved line, whether the two sidewall parts have the same shape) of the bottom part and the sidewall parts.

From the viewpoint of ease of handling of the hollow fiber, an angle (hereinafter referred to as "rising angle") formed by the bottom part and the sidewall parts of the cross section of the support is preferably greater than 0 degrees and equal to or less than 90 degrees, and more preferably equal to or greater than 20 degrees and equal to or less than 90 degrees. In the case of the support in the cross section of which the bottom part is a point illustrated in FIGS. 3(b) and 3(c), the rising angle is perpendicular to a bisector of an angle formed by the two sidewall parts, and refers to an angle of the sidewall parts with respect to a straight line passing through the bottom part. When the sidewall parts are curved, the rising angle refers to an angle formed with a straight line connecting ends of the sidewall parts and the middle of the bottom part and the bottom part.

The cross-sectional shape of the support is preferably a C shape, a U shape, or a V shape. When the cross-sectional shape is the U shape or the V shape, the support is substantially made up of the sidewall parts. For this reason, when the hollow fiber is placed, the hollow fiber may be in contact with only the sidewall parts instead of the bottom part of the support 10.

According to the hollow fiber cryopreservation instrument 2 of the present embodiment, the support 10 has the sidewall parts 12 and 13, thus the cells can be cooled or heated in a more favorable state in addition to improving the handleability of the hollow fiber.

Third Embodiment

A hollow fiber cryopreservation instrument of the present embodiment includes a long support on which a hollow fiber is placed. The support is formed of a low-temperature-resistant material. The support has a bottom part for placing the hollow fiber, and sidewall parts that rise from the bottom part in a longitudinal direction of the support. Through-holes are formed in the support. A description is not given of items in common with the hollow fiber cryopreservation instruments of the first and second embodiments.

Figure 4:
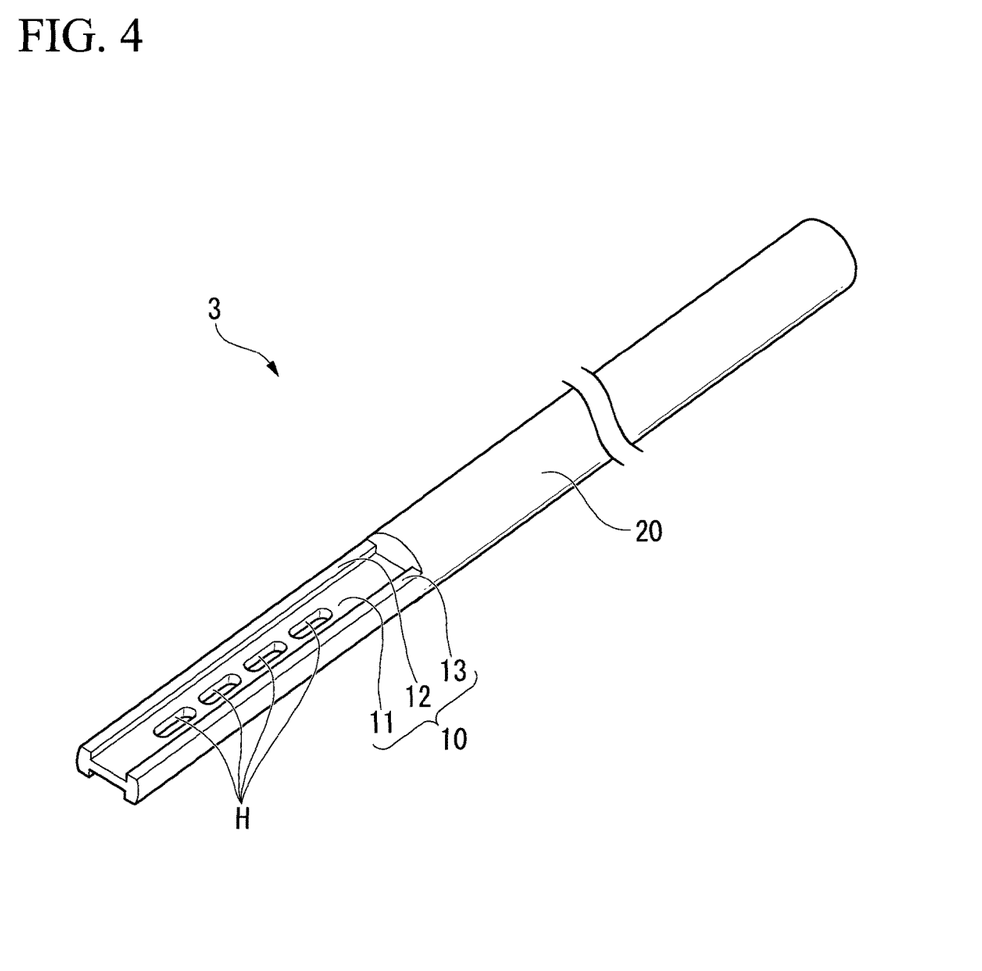
FIG. 4 is a perspective view illustrating an embodiment of the hollow fiber cryopreservation instrument according to the present invention.

FIG. 4 is a perspective view illustrating an embodiment of a hollow fiber cryopreservation instrument according to the present invention. A hollow fiber cryopreservation instrument 3 includes a long support 10 on which a hollow fiber is placed. A rod-like handle 20 serving as a handle is formed at one end of the support 10. The support 10 has a bottom part 11, and sidewall parts 12 and 13 that rise from the bottom part in a longitudinal direction of the support. Through-holes H are formed in the bottom part 11 of the support 10. The through-holes H formed in the support 10 pass through the hollow fiber side on which the hollow fiber is placed, and the side opposite to the hollow fiber side. In the present embodiment, the through-holes H are formed in the support in a direction that faces the hollow fiber placed on the support.

In the case of a commercially available exclusive instrument for cryopreserving cells, it is not assumed that the hollow fiber is placed, and thus there is a problem that it is not considered to effectively bring the hollow fiber into contact with a gas and to quickly cool the cells in the hollow fiber. However, as in the present invention, the through-holes H are formed in the bottom part 11 of the support 10. Thereby, since the hollow fiber is easily exposed to cold air or heat from the outside, the cells included in the hollow fiber can be more quickly cooled or heated.

Here, the through-holes H formed in the support are formed to pass through the hollow fiber side on which the hollow fiber is placed, and the side opposite to the hollow fiber side. Thereby, since the cold air or the heat from the outside is easily directly transferred to the hollow fiber, the cells included in the hollow fiber can be more quickly cooled or heated.

When the hollow fiber is placed on the hollow fiber cryopreservation instrument 3 of the present embodiment, a longitudinal direction of the support 10 and a longitudinal direction of the hollow fiber become nearly the same direction, and the hollow fiber can be placed on the support 10.

The through-holes are formed in a plate thickness direction of the plate-like support as illustrated in FIG. 4 should be understood as the through-holes are formed in the direction that faces the hollow fiber placed on the support.

In a hollow fiber cryopreservation method, from the viewpoint of reliably including the cells in the hollow fiber, the cells are preferably included in nearly the middle of the hollow fiber in the longitudinal direction of the hollow fiber. For example, a layer of only a culture fluid of the cells, a gas layer, a liquid layer including the cells and the culture fluid, a gas layer, and a layer of only the culture fluid are preferably formed in an internal space of the hollow fiber starting from an end side of the hollow fiber. Therefore, as illustrated in FIG. 4, the through-holes H are preferably formed in nearly the middle of the support 10 in the longitudinal direction of the support 10. The through-holes H are formed in nearly the middle of the support 10 in the longitudinal direction of the support 10, and thereby the cold air or the heat from the outside is easily directly transferred to the hollow fiber. Since the through-holes are not formed at opposite end sides of the support 10 in the longitudinal direction of the support 10 as illustrated in FIG. 4, the rigidity of the entire support is enhanced. In addition, workability when the hollow fiber is placed on the support is also favorable.

In the present embodiment, the case in which the plurality of through-holes H are formed in a part of the bottom part 11 of the support 10 is given as an example. However, within a range in which a function of placing the hollow fiber is not hindered, one through-hole H may be formed in the support, or a plurality of through-holes H may be formed in the entire support. When the support has the bottom part and the sidewall parts, the through-holes H may be formed only in the bottom part as shown in the above hollow fiber cryopreservation instrument 3, or conversely, may be formed only in the sidewall parts. Shapes of the through-holes H are not particularly limited. A shape of the support 10 in which the through-holes H are formed may be formed to be, for example, a mesh shape, a net shape, or a ladder shape.

According to the hollow fiber cryopreservation instrument 3 of the present embodiment, the through-holes H are formed in the support 10, and thereby the cells can be more favorably cooled or heated.

Fourth Embodiment

A hollow fiber cryopreservation instrument of the present embodiment includes a long support on which a hollow fiber is placed. The support is formed of a low-temperature-resistant material. The support has a bottom part for placing the hollow fiber. Through-holes passing through the side on which the hollow fiber is placed and the side opposite to the side at which the hollow fiber is placed are formed in the support. A description is not given of items in common with the hollow fiber cryopreservation instruments of the first to third embodiments.

Figure 5:
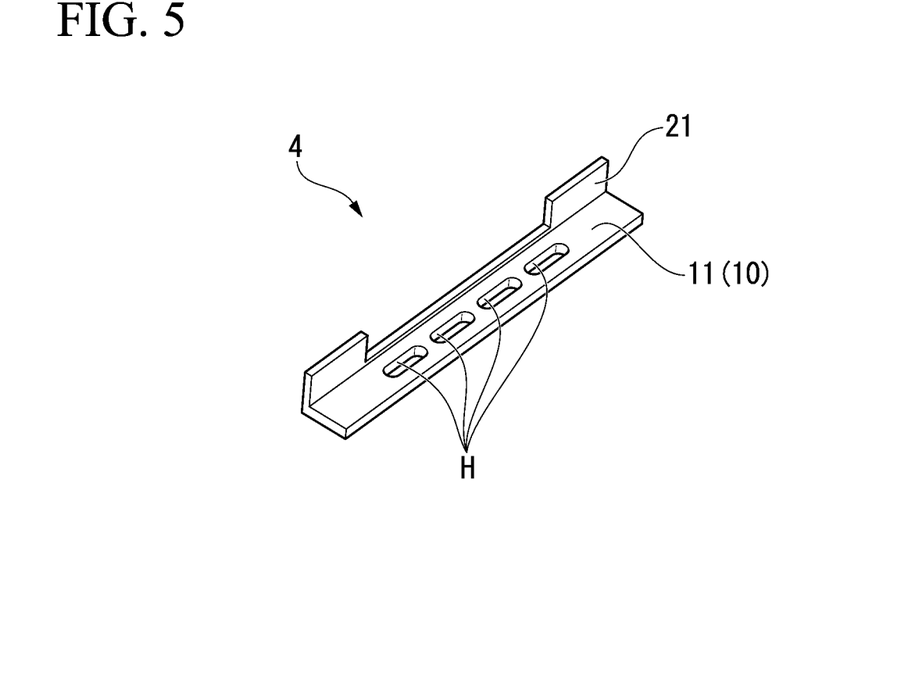
FIG. 5 is a perspective view illustrating an embodiment of the hollow fiber cryopreservation instrument according to the present invention.

FIG. 5 is a perspective view illustrating an embodiment of a hollow fiber cryopreservation instrument according to the present invention. A hollow fiber cryopreservation instrument 4 includes a long support 10 on which a hollow fiber is placed. Through-holes H are formed in a bottom part 11 of the support 10. Plate-like protrusions 21 serving as handles are formed at ends of the bottom part 11 of the support 10. The protrusions 21 can be easily grasped by tweezers. As illustrated in FIG. 5, when the protrusions 21 constitute a sidewall rising from the bottom part in a longitudinal direction of the support, the protrusions 21 shall constitute a sidewall part doubling as the handles.

According to the hollow fiber cryopreservation instrument 4 of the present embodiment, since a length of the support 10 and a length of the hollow fiber cryopreservation instrument are the same, the storability of the entire hollow fiber cryopreservation instrument is excellent.

«Cell Cryopreservation Method»

A cell cryopreservation method of the present invention has a process (a process A) of placing a hollow fiber, in an internal space of which cells are included, on a support of the hollow fiber cryopreservation instrument of the present invention, and a process (a process D) of cryopreserving the cells in a state in which the hollow fiber is placed on the support. Hereinafter, the cell cryopreservation method of the present embodiment will be described, but the cell cryopreservation method of the present invention is not limited to the following embodiments.

First Embodiment

A cell cryopreservation method of the present embodiment has a process (a process A) of placing a hollow fiber, in an internal space of which germ cells are included, on a support of a hollow fiber cryopreservation instrument, a process (a process B) of storing the support on which the hollow fiber is placed in a protective container after the process A, a process (a process C) of cooling the hollow fiber, in the internal space of which the germ cells are included, and freezing the cells, and a process (a process D) of cryopreserving the cells in a state in which the hollow fiber is placed on the support after the processes A, B and C. In the cell cryopreservation method of the present invention, the processes B and C are not essential processes.

In the present embodiment, the cells included in the internal space of the hollow fiber are germ cells and/or stem cells. The germ cells are a comprehensive concept including primordial germ cells, spermatozoa, or sperm cells, ova, oocytes, and early embryos. Here, the sperm cells refer to precursor cells in a process of becoming the spermatozoa.

The oocytes refer to precursor cells in a process of becoming the ova. The early embryos refer to pre-implantation fertilized ova. The stem cells include ES cells, iPS cells, tissue stem cells, or the like.

The cells may be included in the internal space of the hollow fiber in a state of a cell mass or a cell tissue, and may be, for example, a state of a spheroid, an organoid, an early embryo. The spheroid refers to a plurality of cells aggregated into a three-dimensional state. The organoid refers to a cell tissue body self-organized by integrating cells in a controlled space at high density.

A membrane forming the hollow fiber includes polysulfone, polyethersulfone, polyacrylonitrile, polyamide, polyethylene, polypropylene, cellulose acetate, regenerated cellulose, or the like. To contain and cryopreserve the germ cells, particularly, cellulose acetate is preferable, and cellulose diacetate is more preferable.

Figure 6:
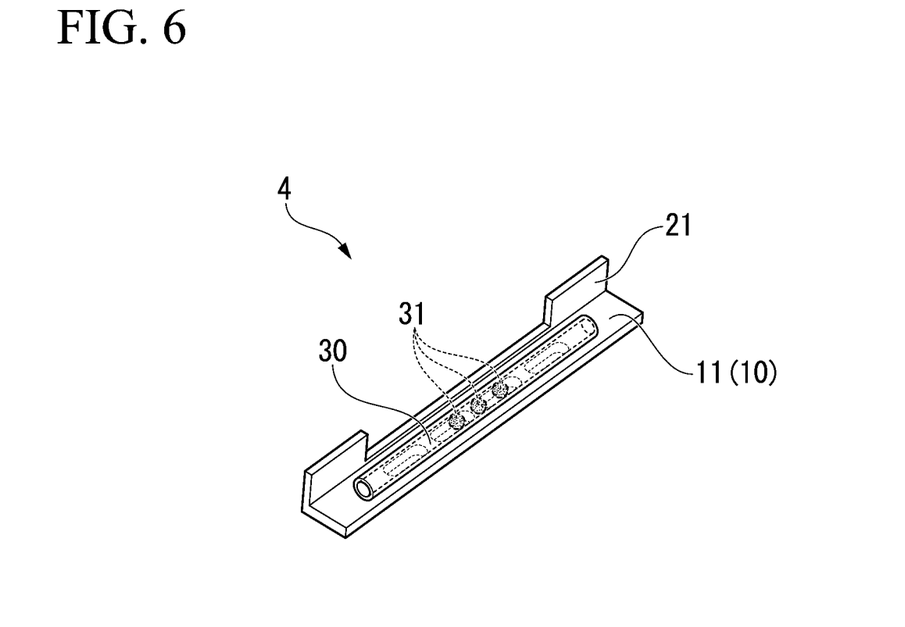
FIG. 6 is a schematic view illustrating processes of an embodiment of a cell cryopreservation method according to the present invention.
Figure 7:
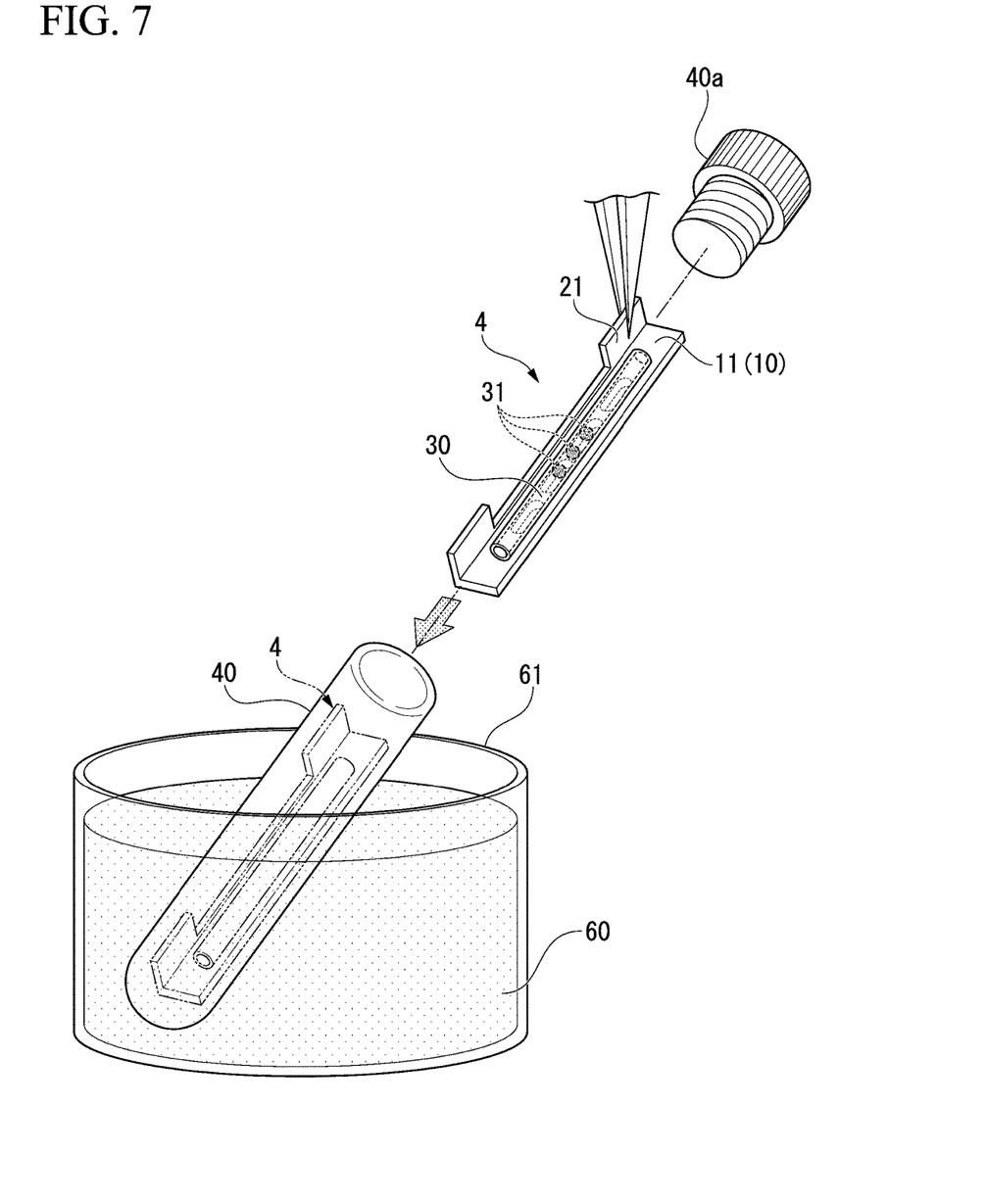
FIG. 7 is a schematic view illustrating processes of an embodiment of the cell cryopreservation method according to the present invention.
Figure 8:
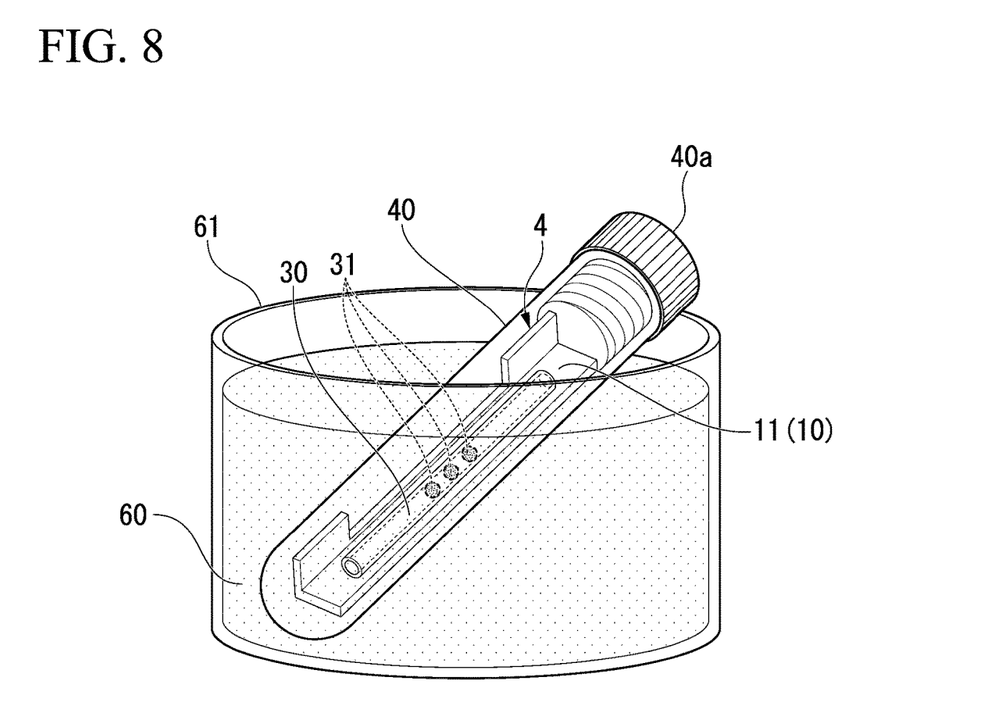
FIG. 8 is a schematic view illustrating processes of an embodiment of the cell cryopreservation method according to the present invention.

FIGS. 6 to 8 are schematic diagrams illustrating processes of the cell cryopreservation method of the present embodiment.

A method of obtaining the hollow fiber, in the internal space of which the germ cells are included, is known. The hollow fiber, in the internal space of which the germ cells are included, can be obtained according to a method described in, for example, U.S. Pat. No. 5,051,716.

The hollow fiber 30 may be previously immersed in a cryopreservation solution before being placed on the support 10. Thereby, when the germ cells are introduced into the internal space of the hollow fiber, a first liquid such as a culture fluid introduced along with the germ cells or an intracellular fluid of the germ cell is replaced with a cryopreservation solution. The cryopreservation solution is a liquid suitable for cryopreservation. The cryopreservation method of the germ cells includes quick freezing in a high concentration of freezing damage protecting fluid, normal freezing in a low concentration of freezing damage protecting fluid, slow freezing for cooling the cells at a slow cooling speed for a long time, and so on. The cell cryopreservation method of the present invention can be applied to any freezing method. The quick freezing in a high concentration of freezing damage protecting fluid is also called vitrification. In addition, the freezing damage protecting fluid is also called a vitrification solution. Vitrification freezing is a preferred freezing method from the viewpoint of cell viability. An intracellular protection type vitrification solution includes a dimethyl sulfoxide (DMSO)-containing liquid, an ethylene glycol-containing liquid, a propanediol-containing liquid, and so on. The intracellular protection type vitrification solution includes a sucrose-containing liquid, a trehalose-containing liquid, a Ficoll-Conrey solution, an ε-poly-L-lysine (PLL)-containing liquid, an ε-poly-D-lysine-containing liquid, an α-poly-L-lysine-containing liquid, an α-poly-D-lysine-containing liquid, and so on.

To replace the first liquid included in the internal space of the hollow fiber with the vitrification solution, a plurality of mixtures obtained by mixing the vitrification solution and the first liquid such as the culture fluid at a ratio that provides a moderate concentration gradient may be used as a second liquid. That is, a plurality of kinds of second liquids in which a concentration of the vitrification solution is gradually increased may be used. As the number of kinds of the second liquid having a concentration gradient increases, the first liquid or the intracellular fluid of the germ cell included in the internal space of the hollow fiber can be replaced with the vitrification solution in mild conditions. However, when there are too many, a task is complicated, and thus two to five kinds of second liquids are typically used.

When the plurality of kinds of the second liquids are used, the hollow fiber is dipped into the second liquid in which the concentration of the vitrification solution is low. The replacement is performed for a predetermined time while stirring the second liquid as needed. As described above, the holes of the hollow fiber do not allow the passage of the germ cells, but allow the passage of the first liquid and the second liquid. Therefore, the internal space of the hollow fiber or the intracellular fluid of the germ cell is replaced from the first liquid to the second liquid. On this occasion, the germ cells are maintained in a state in which they are included in the internal space of the hollow fiber. This is sequentially performed starting from the second liquid in which the concentration of the vitrification solution is low, and thereby the first liquid or the intracellular fluid of the germ cell in the internal space of the hollow fiber can be replaced with the vitrification solution.

(Process A)

As illustrated in FIG. 6, the hollow fiber 30, in the internal space of which the germ cells 31 are included and which is immersed in the cryopreservation solution is placed on the support 10 of the hollow fiber cryopreservation instrument 4 (a process A). The hollow fiber 30 can be visually handled using tweezers.

(Processes B and C)

After the process A, the hollow fiber 30, in the internal space of which the germ cells 31 are included, is cooled (a process C). As illustrated in FIG. 7, the cooling of the hollow fiber is performed by introducing the support 10 and the hollow fiber 30 placed on the support 10 into a pre-cooled tubular protective container 40 (a process B). The tubular protective container 40 is placed in an ultralow-temperature vapor atmosphere by previously inputting a part of the tubular protective container 40 into a container 61 in which liquid nitrogen 60 is stored and cooling a gas in the tubular protective container 40.

The germ cells 31 included in the hollow fiber 30 along with the vitrification solution is frozen by the ultralow-temperature vapor atmosphere in the tubular protective container 40. For example, from the viewpoint of making easy acquisition not possible, as with human cells, and inhibiting bacterial contamination, the hollow fiber is frozen in the low-temperature or ultralow-temperature vapor atmosphere as shown in the present embodiment. However, the hollow fiber is preferably frozen by exposure to liquid nitrogen vapor.

As illustrated in FIG. 8, the support 10 on which the hollow fiber 30 is placed is completely stored in the tubular protective container 40, and then a lid 40a of the protective container is attached. Thereby, the hollow fiber 30 is sealed.

(Process D)

The protective container 40 and the support 10 are integrated, and the hollow fiber 30 that is in a sealed state is cryopreserved in a freezer, liquid nitrogen or liquid helium (a process D).

As described above, the germ cells, which are included and cryopreserved in the internal space of the hollow fiber, are dipped into a heating liquid along with the hollow fiber, and thereby are thawed. Then, when a discharge pressure is applied from one end of the hollow fiber to the internal space, the germ cells are discharged outward from the internal space of the hollow fiber. If the culture is performed with the germ cells included in the internal space of the hollow fiber, the hollow fiber including the germ cells after being thawed may be put into a desired culture medium.

According to the cell cryopreservation method of the present embodiment, since the support 10 on which the hollow fiber 30 is placed is introduced into the pre-cooled tubular protective container 40, and since the support 10 and the hollow fiber 30 placed on the support 10 are cooled, the bacterial contamination or the like can be effectively suppressed. The cell cryopreservation method of the present invention is not limited to the above embodiment.

Hereinafter, other embodiments according to the cell cryopreservation method of the present invention will be described. A description is not given of items in common with the cell cryopreservation method of the first embodiment.

Second Embodiment

A cell cryopreservation method of a second embodiment has a process (a process A) of placing a hollow fiber, in an internal space of which germ cells are included, on the support of the hollow fiber cryopreservation instrument of the present invention, a process (a process B) of storing the support on which the hollow fiber is placed in a tubular protective container after the process A, a process (a process C) of cooling the hollow fiber, in the internal space of which the germ cells are included after the process B and freezing the cells, and a process (a process D) of cryopreserving the cells in a state in which the hollow fiber is placed on the support after the processes A, B and C.

For example, after the hollow fiber 30 is placed on the support 10, and the support 10 on which the hollow fiber 30 is placed is stored in the protective container, the support 10 and the hollow fiber 30 placed on the support 10 may be input into liquid nitrogen along with the protective container 40 in which they are housed, the hollow fiber 30 may be cooled, and then the cells may be cryopreserved.

Third Embodiment

A cell cryopreservation method of a third embodiment has a process (a process A) of placing a hollow fiber, in an internal space of which germ cells are included, on the support of the hollow fiber cryopreservation instrument of the present invention, a process (a process C) of cooling the hollow fiber, in the internal space of which the germ cells are included, to freeze the cells after the process A, a process (a process B) of storing the support on which the hollow fiber is placed in a tubular protective container after the process C, and a process (a process D) of cryopreserving the cells in a state in which the hollow fiber is placed on the support after the processes A, B and C.

Figure 9:
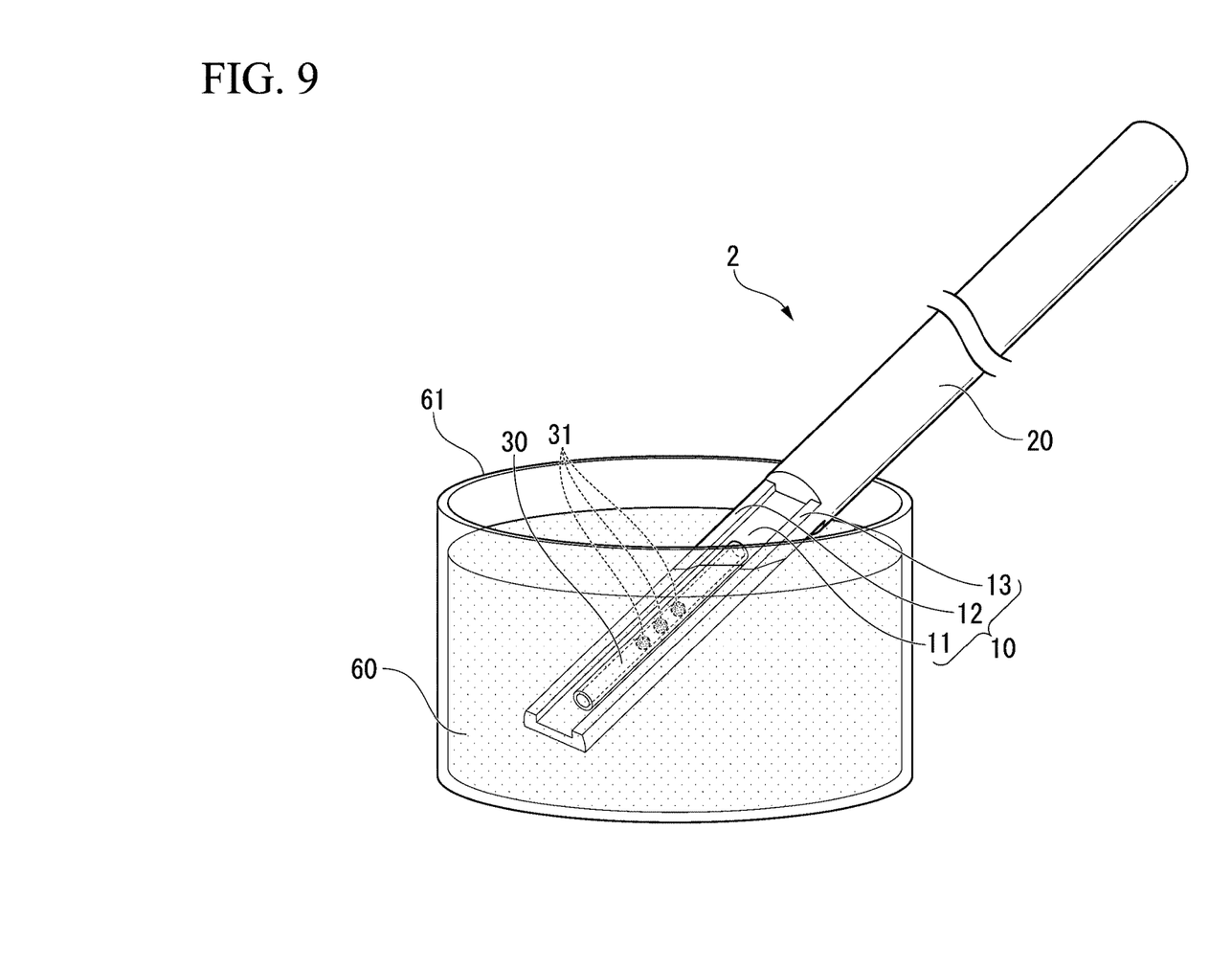
FIG. 9 is a schematic view illustrating processes of an embodiment of the cell cryopreservation method according to the present invention.

For example, when a case in which the hollow fiber cryopreservation instrument 2 is used is given as an example, the hollow fiber 30 may be placed on the support 10, the support 10 on which the hollow fiber 30 is placed may be directly input into liquid nitrogen, the hollow fiber may be cooled to freeze the cells (FIG. 9), the hollow fiber 30 after the freezing may be stored in the tubular protective container 50 (FIG. 10), and then the cells may be cryopreserved. In addition, the support 10 on which the hollow fiber 30 is placed may be exposed to liquid nitrogen vapor, the hollow fiber may be cooled to freeze the cells, the hollow fiber 30 after the freezing may be stored in the tubular protective container 50, and then the cells may be cryopreserved.

Fourth Embodiment

A cell cryopreservation method of a fourth embodiment has a process (a process C) of cooling a hollow fiber, in an internal space of which germ cells are included, to freeze the cells, a process (a process A) of placing the hollow fiber, in the internal space of which the germ cells are included, on the support of the hollow fiber cryopreservation instrument of the present invention after the process C, a process (a process B) of storing the support on which the hollow fiber is placed in a tubular protective container after the processes C and A, and a process (a process D) of cryopreserving the cells in a state in which the hollow fiber is placed on the support after the processes A, B and C.

For example, after the hollow fiber, in the internal space of which the germ cells are included, is previously cooled to freeze the germ cells, the hollow fiber may be placed on the support, and the cells may be cryopreserved in a state in which the hollow fiber is placed on the support.

A case in which the cell cryopreservation methods of the second to fourth embodiments have the process B is given as an example. However, in the cell cryopreservation method of the present invention, the process B is not essential. For example, the process C may be performed after the process A, and then the process D may be performed. Alternatively, the process A may be performed after the process C, and then the process D may be performed.

The cell cryopreservation methods of the first to fourth embodiments have been described with reference to FIGS. 7 to 11 and a case of using the hollow fiber cryopreservation instrument 4 or the hollow fiber cryopreservation instrument 2 is given as an example. However, in the cell cryopreservation method of the present invention, the hollow fiber cryopreservation instrument may be any hollow fiber cryopreservation instrument of the present invention, and for example, the hollow fiber cryopreservation instrument 1 or the hollow fiber cryopreservation instrument 3 of the embodiment may be used.

One embodiment of the present invention provides the use of the hollow fiber cryopreservation instrument of the present invention for freezing the hollow fiber. That is, one embodiment of the present invention includes the long support for placing the hollow fiber, and the support provides the use of the preservation instrument formed of a low-temperature-resistant material for freezing the hollow fiber.

<Protective Container>

The shape of the protective container is not particularly limited, and includes a tubular shape such as a rounded tubular shape or a rectangular tubular shape, or a shape such as a bag shape. In the case of the tubular shape, like the previously exemplified protective containers 40 and 50, the tubular shape is a test tube shape, one end of which is open and is formed with an opening, and the other end of which is closed, which is preferable from the viewpoint of sealability. Similarly, the bag shape is preferably a shape in which an opening is formed in a part of a bag and a part other than the opening is closed. Particularly, when the human cells are cryopreserved, the shape of the protective container is preferably the test tube shape such as the rounded tubular shape or the rectangular tubular shape from the viewpoint of sealability. When multiple hollow fibers are enclosed at one time, the shape of the protective container is preferably the bag shape.

Figure 10:
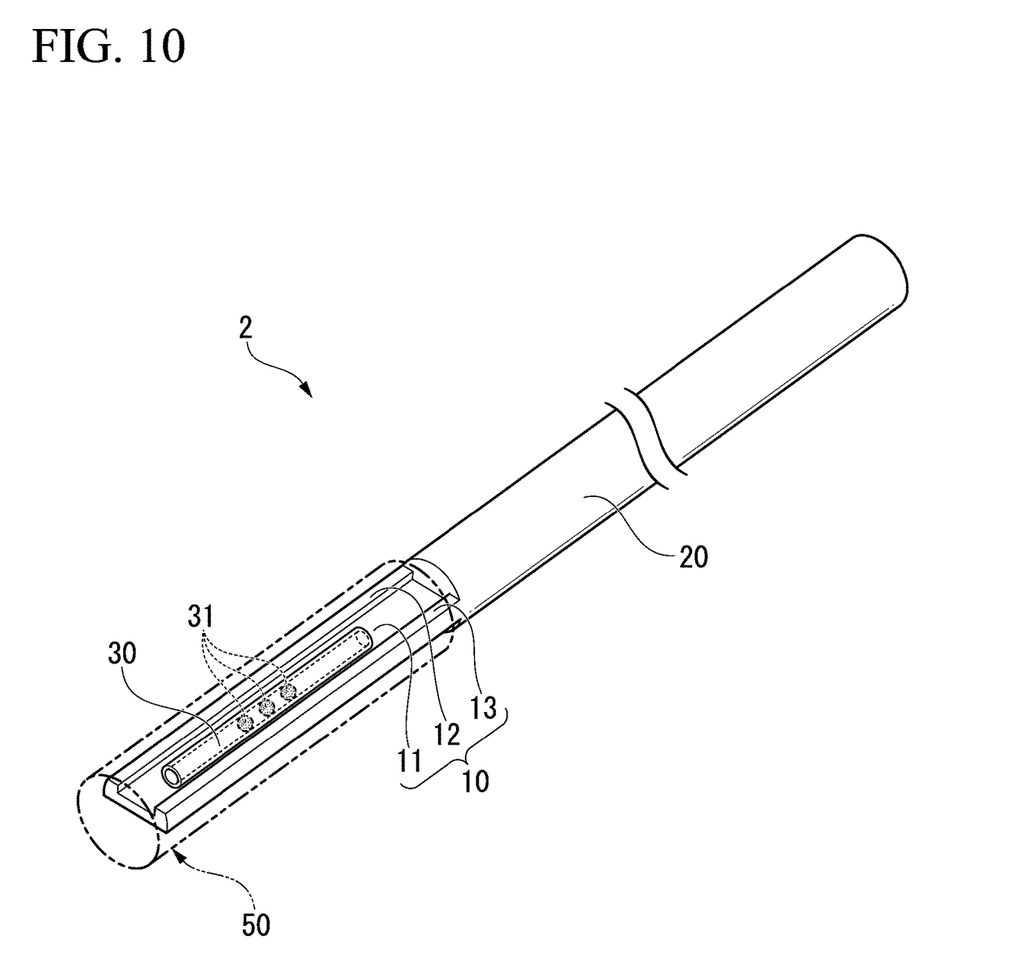
FIG. 10 is a schematic view illustrating processes of an embodiment of the cell cryopreservation method according to the present invention.

The opening of the protective container may be closed by the lid as illustrated in FIG. 8, or be closed by inserting and fitting the hollow fiber cryopreservation instrument as illustrated in FIG. 10. Alternatively, the hollow fiber may be sealed by sealing the entire hollow fiber cryopreservation instrument as illustrated in FIG. 8, or by sealing a part of the hollow fiber cryopreservation instrument as illustrated in FIG. 10. Further, the hollow fiber may be sealed by sealing a part of the support. From the viewpoint of sealability, the entire hollow fiber cryopreservation instrument is preferably sealed.

Figure 11:
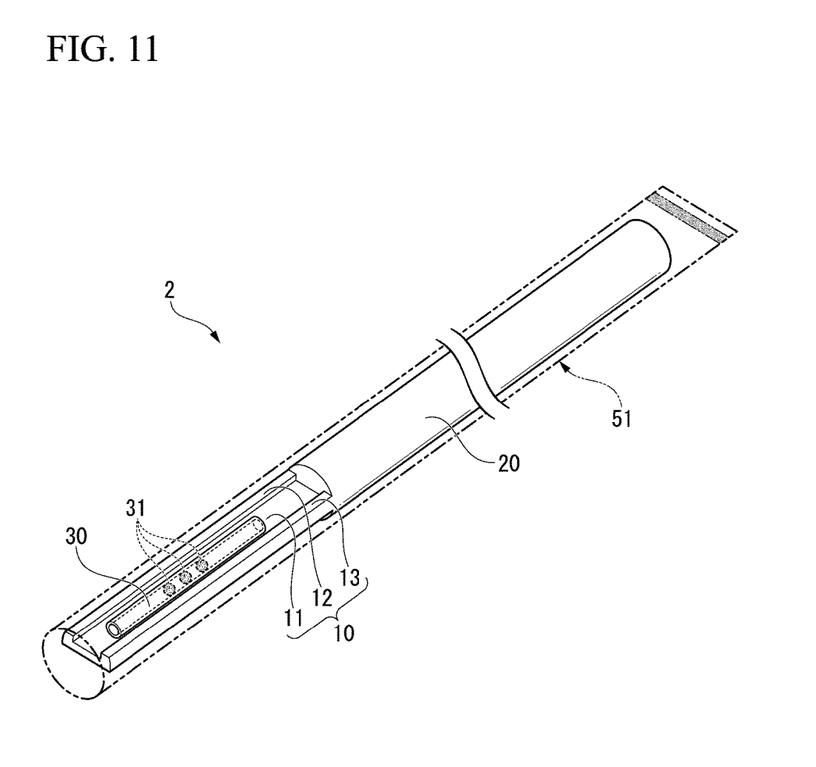
FIG. 11 is a schematic view illustrating processes of an embodiment of the cell cryopreservation method according to the present invention.

For easier sealing in a state in which the handle 20, the support 10, and the entire hollow fiber 30 are enclosed, the protective container is set as the test tube shape, an inner diameter of which is larger than a diameter of an outer circumferential edge of the handle 20, and the opening of the protective container 51 having the test tube shape is closed by a method such as heat sealing after the handle 20, the support 10, and the hollow fiber 30 are stored. Thereby, the entire hollow fiber cryopreservation instrument may be sealed (FIG. 11).

Constitutions in each of the embodiments described above and combinations thereof are merely examples, and additions, omissions, substitutions, and other modifications of the constitutions are possible without departing from the spirit of the present invention. The present invention is not limited by each of the embodiments, but is only limited by the claims.

INDUSTRIAL APPLICABILITY

According to the present invention, a hollow fiber cryopreservation instrument capable of easily cryopreserving a hollow fiber, and a cell cryopreservation method capable of easily cryopreserving a hollow fiber, in the internal space of which cells such as the germ cells are included, can be provided, and widely used in biology-related fields, medical science-related fields, and particularly reproductive medicine fields.

REFERENCE SIGNS LIST 1, 2, 3, 4 Hollow fiber cryopreservation instrument
10 Support
11 Bottom part
12, 13 Sidewall part,
20 Handle,
21 Protrusion
30 Hollow fiber
31 Germ cell
40, 50, 51 Protective container
40a Lid
60 Liquid nitrogen
61 Container

The invention claimed is:

1. A hollow fiber cryopreservation instrument comprising a long support on which a hollow fiber, in an internal space of which cells are included, is placed directly in contact with the support,
wherein the hollow fiber is a membrane formed into a straw shape,
wherein the membrane includes cellulose acetate, cellulose diacetate, or regenerated cellulose,
wherein an inner diameter of the hollow fiber is from 20 μm to 500 μm,
wherein the support is formed of a low-temperature-resistant material,
wherein through-holes passing through a side on which a hollow fiber is placed and a side opposite to the side on which the hollow fiber is placed are formed in the support,
wherein through-holes are not formed at opposite end sides of the support in the longitudinal direction of the support,
wherein the support has a bottom part on which the hollow fiber is placed, and sidewall parts that rise from the bottom part in a longitudinal direction of the support.

2. The hollow fiber cryopreservation instrument according to claim 1, wherein the through-holes are formed in a middle portion of the support in a longitudinal direction of the support.

3. The hollow fiber cryopreservation instrument according claim 1, wherein the support is made of a resin or a metal.

4. The hollow fiber cryopreservation instrument according to claim 1, wherein the low-temperature-resistant material is at least one selected from the group consisting of titanium, aluminum, stainless steel, polyvinyl chloride, polyester, polyimide, polysulfone, polystyrene, polyvinyl acetate, polystyrene, polyurethane, an ABS resin, an AS resin, an acrylic resin, polyethylene, polypropylene, polycarbonate and polytetrafluoroethylene.

5. The hollow fiber cryopreservation instrument according to claim 1,
wherein the support is made of a resin or a metal,
wherein the thickness of the support is formed to 0.01 mm or more and 1 mm or less.

6. A cell cryopreservation method, comprising:
a process of placing a hollow fiber, in an internal space of which cells are included, on a long support of a hollow fiber cryopreservation instrument comprising the support, as the hollow fiber directly in contact with the support,
wherein the hollow fiber is a membrane formed into a straw shape,
wherein the membrane includes cellulose acetate, cellulose diacetate, or regenerated cellulose,
wherein an inner diameter of the hollow fiber is from 20 μm to 500 μm,
wherein the support is formed of a low-temperature-resistant material; and
a process of cryopreserving the cells in a state in which the hollow fiber is placed on the support.

7. The cell cryopreservation method according to claim 6, wherein the cell cryopreservation method includes a process of storing the support, on which the hollow fiber is placed, in a protective container after the process of placing the hollow fiber on the support.

8. The cell cryopreservation method according to claim 6, wherein the cell cryopreservation method includes a process of cooling the hollow fiber to freeze the cells after the process of placing the hollow fiber on the support.

9. The cell cryopreservation method according to claim 6, wherein the cells are germ cells and/or stem cells.

10. The cell cryopreservation method according to claim 6, wherein through-holes passing through a side on which a hollow fiber is placed and a side opposite to the side on which the hollow fiber is placed are formed in the support.

11. The cell cryopreservation method according to claim 10, wherein the through-holes are formed in a middle portion of the support in a longitudinal direction of the support.

12. The cell cryopreservation method according to claim 6, wherein the support has a bottom part on which the hollow fiber is placed, and sidewall parts that rise from the bottom part in a longitudinal direction of the support.

13. The cell cryopreservation method according to claim 6, wherein the support is made of a resin or a metal.

14. The cell cryopreservation method according to claim 6,
wherein through-holes passing through a side on which a hollow fiber is placed and a side opposite to the side on which the hollow fiber is placed are formed in the support,
wherein the through-holes are not formed at opposite end sides of the support in the longitudinal direction of the support.

15. The cell cryopreservation method according to claim 6,
wherein through-holes passing through a side on which a hollow fiber is placed and a side opposite to the side on which the hollow fiber is placed are formed in the support,
wherein short diameters of the through-holes are larger than an inner diameter of the placed hollow fiber.

* * * * *